United States Patent [19]

Duer

[11] Patent Number: 5,946,089

[45] Date of Patent: Aug. 31, 1999

[54] PLASMA SPECTROMETER WITH SHUTTER ASSEMBLY

[75] Inventor: Reuven Duer, Karkur, Israel

[73] Assignee: Jordan Valley Applied Radiation Ltd., Migdal Ha'emek, Israel

[21] Appl. No.: 09/114,603

[22] Filed: Jul. 13, 1998

[51] Int. Cl.⁶ .................................................. G01N 21/63
[52] U.S. Cl. ........................ 356/318; 359/507; 359/509
[58] Field of Search ........................... 356/318; 359/507, 359/508, 509; 219/121.75

[56] References Cited

U.S. PATENT DOCUMENTS

| | | | |
|---|---|---|---|
| 3,571,554 | 3/1971 | Baujoin | 359/507 |
| 4,191,475 | 3/1980 | Sourrouille | 356/318 |
| 4,925,307 | 5/1990 | Cremers et al. | 356/318 |
| 4,986,658 | 1/1991 | Kim | 356/318 |
| 5,312,397 | 5/1994 | Cosmescu | 604/389 |
| 5,379,103 | 1/1995 | Zigler | 356/73 |

*Primary Examiner*—P. L. Evans
*Attorney, Agent, or Firm*—Lahive & Cockfield, LLP

[57] ABSTRACT

Apparatus for optical analysis of a sample, including an energy source, which generates a pulse of energy that is incident on the sample, causing the sample to emit radiation characteristic of the composition of the sample, and a detector assembly, which receives and analyzes the radiation emitted by the excited sample. An optical assembly conveys the emitted radiation from the sample to the detector assembly, the optical assembly including an optic proximal to the sample, on which optic the radiation is incident along a beam path thereof between the sample and the detector assembly. A moving mechanical element moves in synchronization with the pulse from the energy source so as to substantially prevent matter ejected from the sample responsive to the incident energy from accumulating on the optic.

25 Claims, 4 Drawing Sheets

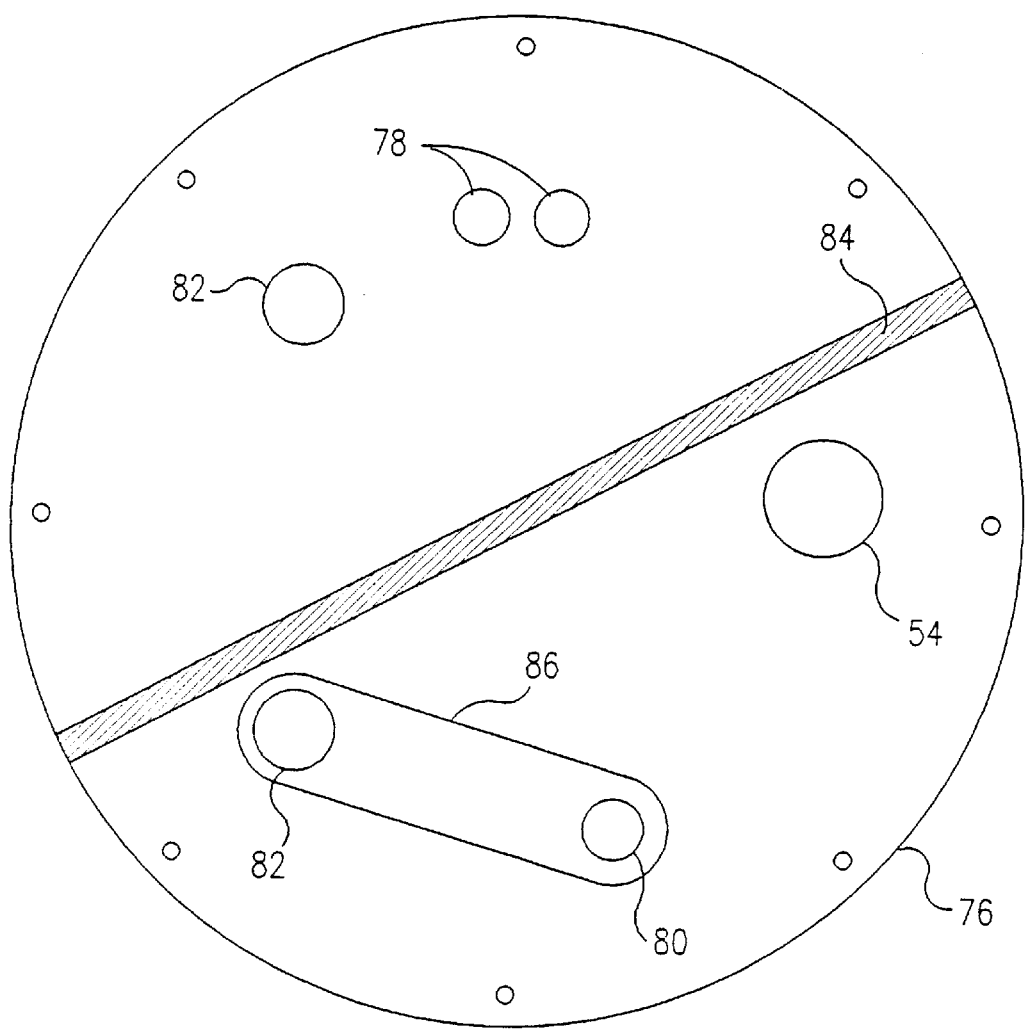

PLASMA SPECTROMETER WITH SHUTTER ASSEMBLY

FIELD OF THE INVENTION

The present invention relates generally to optical instruments and methods, and specifically to optical instrumentation for use in laser plasma spectroscopy.

BACKGROUND OF THE INVENTION

Laser-induced plasma spectroscopy (LIPS) is a method known in the art for analysis of elements present in a sample, typically a liquid sample. Apparatus and methods for LIPS are described, for example, in U.S. Pat. No. 4,925,307, to Cremers et al., and in U.S. Pat. No. 5,379,103, to Zigler, both of which are incorporated herein by reference.

In a typical LIPS system, a high-intensity pulsed laser beam is focused at or near an upper surface of the sample, creating a breakdown spark. The spark causes a plasma cloud to be blown off the sample. Excited elements from the sample in the plasma cloud emit characteristic spectral radiation. A portion of the emitted radiation is collected by an optical system and focused into a spectrometer and optical detector. A spectrum of the radiation is analyzed to determine the elemental composition of the sample.

The plasma cloud formation is typically accompanied by a shock wave propagating off the sample at high, even supersonic, speed. Particles from the sample are sprayed in all directions and may impinge on elements of the optical system. These elements must therefore be cleaned frequently if the LIPS system is to work properly.

SUMMARY OF THE INVENTION

It is an object of some aspects of the present invention to provide improved apparatus and methods for laser-induced plasma spectroscopy (LIPS).

It is a further object of some aspects of the present invention to provide an improved optical assembly for use in dirty environments.

It is still a further object of some aspects of the present invention to provide a self-cleaning optical assembly.

In preferred embodiments of the present invention, apparatus for LIPS comprises a laser, which generates a train of output pulses that are focused onto a sample, creating a plasma from which radiation characteristic of the composition of the sample is emitted. The radiation is collected by an optical assembly, comprising an optic proximal to the sample, such as an objective lens or window. The radiation passes through the optic to a detector assembly, which is used to determine an emission spectrum of the plasma. As described above, matter, i.e., debris or particles, is typically ejected from the sample in the area of the plasma toward the proximal optic. A moving mechanical element, associated with the proximal optic, moves synchronously with the pulse from the laser so as to substantially prevent the ejected matter from accumulating on the optical element.

In some preferred embodiments of the present invention, the mechanical element comprises a movable mount, such as a turntable, on which the proximal optic is mounted. During the laser pulses, the mount positions the optic in an open position, along an optical beam path of the apparatus, in which position the radiation emitted by the plasma can pass through the optic to the detector assembly. In the open position, the matter from the plasma strikes and, at least in part, is deposited on the optic. Therefore, between one laser pulse and the next, the mount moves the optic through one or more closed positions in which the matter emitted from the sample is cleaned off the optic. Preferably, the optical assembly includes two or more proximal optics, which are positioned in the beam path in respective open positions in alternation, so that while one of the optics is in the process of being cleaned, the other optic is available for use in the open position. The optic need not be held stationary in the open or closed positions, but may rather move continuously through one or more of the positions. Preferably, the process of moving and cleaning the optic or optics proceeds continually, in synchronization with a train of the laser pulses, as long as the sample is to be analyzed.

In other preferred embodiments of the present invention, the mechanical element comprises a high-speed shutter. While the laser beam is fired, the shutter is open, so that the radiation emitted by the plasma can pass through the proximal optic. Immediately after the laser pulse, however, the shutter is closed at sufficient speed so that the matter from the plasma does not reach the optic, but rather strikes a surface of the shutter. Preferably, the shutter comprises a rotating beam chopper placed between the sample and the proximal optic, wherein the rotation of the chopper is suitably synchronized with the laser beam. Alternatively, the shutter may open and shut in a reciprocal (back and forth) motion, or may be of any other suitable type known in the art. Further alternatively, the optic itself may be mounted to rotate rapidly for this purpose.

Although preferred embodiments of the present invention are described herein with reference to transmissive optics, i.e., wherein the proximal optic comprises a window or lens, it will be appreciated that the principles of the present invention may be applied to prevent the accumulation of debris or particles on reflective optics, as well, particularly when working with a pulsed source of radiation. Furthermore, it will be appreciated that the principles of the present invention are applicable not only to LIPS, but to other techniques of spectroscopy and optical detection using pulsed radiation, and in other optical systems for use in dirty environments.

There is therefore provided, in accordance with a preferred embodiment of the present invention, apparatus for optical analysis of a sample, including:

an energy source, which generates a pulse of energy that is incident on the sample, causing the sample to emit radiation characteristic of the composition of the sample;

a detector assembly, which receives and analyzes the radiation emitted by the excited sample; and an optical assembly, which conveys the emitted radiation from the sample to the detector assembly, the optical assembly including:

an optic proximal to the sample, on which optic the radiation is incident along a beam path thereof between the sample and the detector assembly; and a moving mechanical element, whose movement is synchronized with the pulse from the energy source so as to substantially prevent matter ejected from the sample responsive to the incident energy from accumulating on the optic.

In a preferred embodiment, the moving mechanical element includes a shutter, which is opened to allow the radiation to pass from the sample to the detector assembly, and which closes immediately following the pulse with sufficient speed so that the matter ejected from the sample substantially does not impinge on the optic. Preferably, the shutter includes a rotating platform, having an aperture which intercepts the beam path when the pulse is incident on the sample.

In another preferred embodiment, the optical assembly includes a cleaning device for cleaning the ejected matter from the optic, and the moving mechanical element includes a platform on which the optic is mounted and which positions the optic in proximity to the cleaning device after the pulse to remove the ejected matter therefrom. Preferably, the platform rotates between an open position, in which the optic is positioned along the beam path, and a closed position, in which the optic is positioned in proximity to the cleaning device.

Preferably, the apparatus includes a trigger device, which senses that the platform is in the open position and sends a trigger signal to the energy source responsive thereto, causing the energy source to generate the pulse. Further preferably, the platform rotates continually between the open and closed positions, and the energy source generates a train of pulses responsive to the trigger signal and synchronized with the rotation of the platform.

Preferably, the cleaning device directs a solvent wash toward a surface of the optic on which the matter accumulates and dries the surface after the solvent wash.

Preferably, the energy source includes a laser.

There is further provided, in accordance with a preferred embodiment of the present invention, apparatus for spectral analysis of a sample, including:

an energy source, which generates a train of pulses of energy that is incident on the sample, causing the sample to emit radiation characteristic of the composition of the sample;

a detector assembly, which receives and analyzes the radiation emitted by the excited sample;

an optic proximal to the sample, on which optic the radiation is incident along a beam path thereof between the sample and the detector assembly; and a cleaning device, which removes matter ejected onto the optic from the sample due to the pulses, the cleaning device operating intermittently, between one pulse and the next in the pulse train.

Preferably, the cleaning device includes a solvent wash, which is directed at a surface of the optic onto which the matter is ejected. Further preferably, the cleaning device dries the optic after the solvent wash.

Preferably, the apparatus includes a turntable on which the optic is mounted, which rotates in synchronization with the pulse train to move the optic between an open position in which the optic is positioned on the beam path and a closed position in which the optic is adjacent to the cleaning device.

There is also provided, in accordance with a preferred embodiment of the present invention, a self-cleaning optical assembly for conveying energy along a beam path, including:

a moving platform, having an open position and one or more closed positions;

an optic mounted on the platform, so that in the open position, the optic intercepts the beam path; and a cleaning device, which cleans the optic when the platform is in the closed position.

Preferably, the moving platform rotates about an axis therethrough, so as to cycle in alternation between the open and closed positions, wherein the rotation of the platform is most preferably synchronized with a pulsed energy source, which emits the energy along the beam path. Further preferably, the assembly includes a trigger device, which triggers the pulsed energy source responsive to the movement of the platform.

Preferably, the cleaning device directs a solvent wash at a surface of the optic when the platform is in one of the closed positions and dries the surface after the solvent wash. Most preferably, the moving platform rotates continually between the open position, the closed position in which the solvent wash is directed at the surface, and another one of the one or more closed positions in which the cleaning device dries the surface.

In a preferred embodiment, the optic includes two optics mounted on the platform in locations that are generally diametrically opposed, and the assembly is configured so that while one of the optics is washed, the other is dried.

There is moreover provided, in accordance with a preferred embodiment of the present invention, a method for spectral analysis of a sample, including:

irradiating the sample with a pulse of energy, so that the sample emits radiation characteristic of the composition of the sample;

collecting the radiation emitted by the sample along a beam path intercepting an optic; and moving an element in the beam path so as to prevent accumulation of matter ejected from the sample on the optic.

Preferably, moving the element includes moving an element in synchronization with the pulse of energy. Further preferably, moving the element in the beam path includes positioning the optic opposite a cleaning device and operating the cleaning device to remove the matter from the optic.

In a preferred embodiment, moving the element includes moving a shutter to block the beam path to the optic after at least a portion of the radiation has passed therethrough but before the matter reaches the optic.

The present invention will be more fully understood from the following detailed description of the preferred embodiments thereof, taken together with the drawings in which:

BRIEF DESCRIPTION OF THE DRAWINGS

FIG. 4 is a schematic top view of a lower surface of the optical assembly of FIGS. 2 and 3.

DETAILED DESCRIPTION OF PREFERRED EMBODIMENTS

Figure 1:
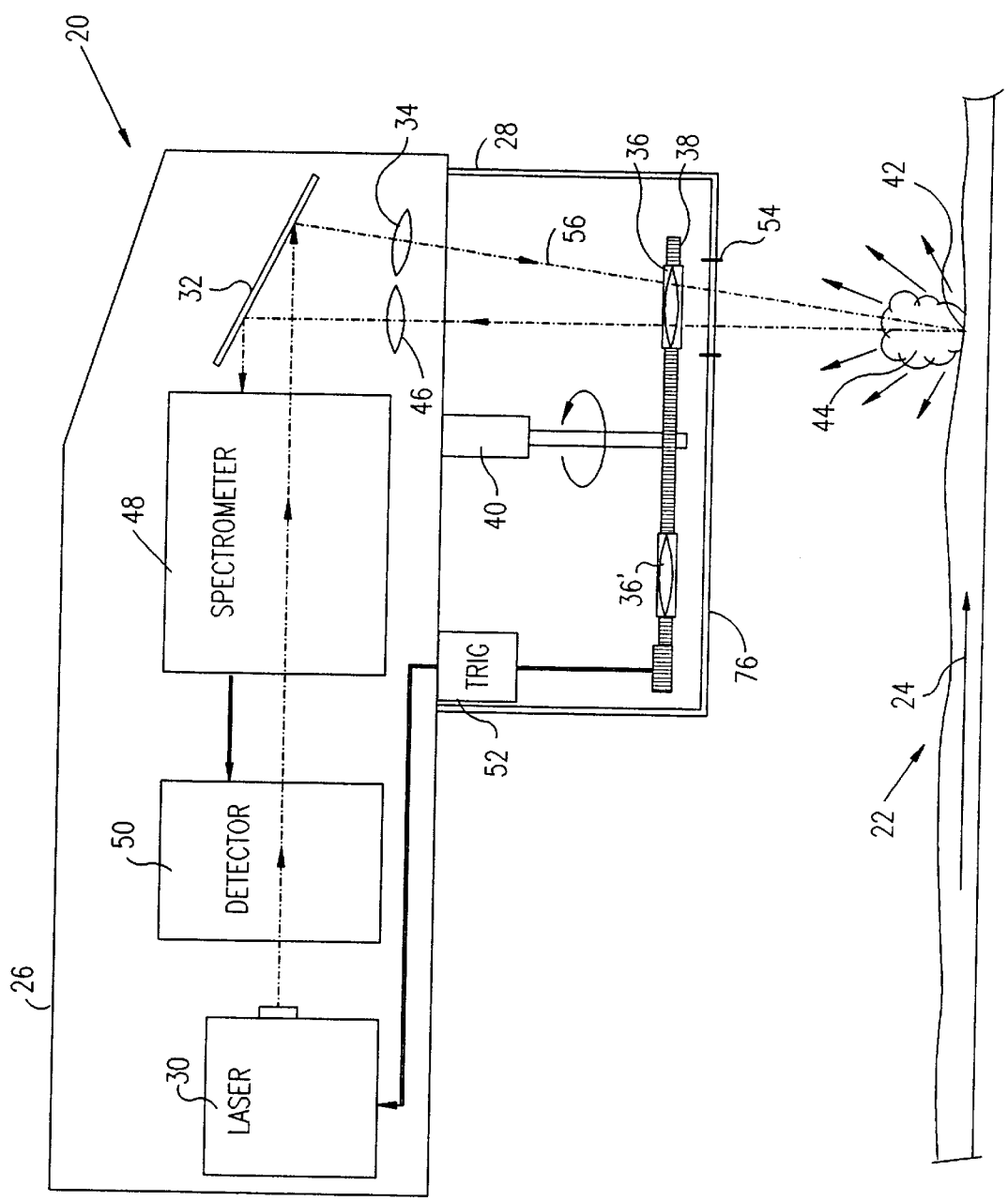
FIG. 1 is a schematic illustration of a system for laser-induced plasma spectroscopy (LIPS), in accordance with a preferred embodiment of the present invention.

Reference is now made to FIG. 1, which is a schematic illustration of a LIPS system 20, in accordance with a preferred embodiment of the present invention. System 20 is preferably used to measure the elemental composition of a stream of sample material 22, which moves along a conveyor beneath system 20 as indicated by an arrow 24.

System 20 comprises a console 26 and an optical assembly 28. The console comprises a laser 30, preferably a Nd:YAG laser, which fires a train of high-intensity pulses. Alternatively, another source of high-energy pulsed radiation may be used. The laser pulses are reflected by a mirror 32 and are focused by a lens 34 through a first window 36 onto sample 22. While laser 30 is firing, window 36 is aligned with an aperture 54 in a lower surface 76 of assembly 28. Window 36 and a second, substantially identical window 36', which preferably comprise fused silica, are mounted on a turntable 38 in assembly 28. Turntable 38 is rotated by a motor assembly 40, so that windows 36 and 36'are positioned in alternation along a path 56 of the laser beam.

When the laser beam strikes sample 22, it creates a breakdown spark at a point 42 on the sample, forming an expanding plasma 44, as well as scattering debris back toward window 36. Radiation emitted by plasma 44 passes through the window and is focused by a collecting lens 46 onto an entrance aperture of a spectrometer 48. A detector 50, preferably a photodiode array (PDA), is coupled to an exit aperture of the spectrometer so as to sense the plasma emission as a function of wavelength. Spectral data from the detector are used in determining the sample's elemental composition, as described, for example, in the above-mentioned U.S. Pat. Nos. 4,925,307 and 5,379,103.

As turntable 38 rotates, a trigger 52 senses the turntable's rotational position and sends a trigger pulse to laser 30 when window 36 or 36' is suitably aligned with aperture 54. Thus, the rotation of the turntable is synchronized with the laser pulse train, and the laser fires only when window 36 or 36' is suitably positioned. Preferably, the rotation of the turntable is further synchronized with a mechanism for washing the debris off the windows, as shown and described below with reference to FIGS. 2, 3 and 4. (For simplicity of illustration, the washing mechanism is not shown in FIG. 1.)

In another preferred embodiment of the present invention, however, motor assembly 40 rotates turntable 38 with sufficient speed so that optics 36 and 36' are moved out of alignment with aperture 54 before the debris can reach the optics. Since some of the debris may be ejected from sample 22 at supersonic speed, very rapid rotation of the turntable is required, generally fast enough to displace the optics at a speed of one hundred to several hundred m/sec, depending on the geometry of the optics and their distance from the sample. Alternatively, optic 36 may be stationary, and motor assembly 40 may be coupled to operate a shutter, such as a rotating optical chopper (not shown in the figures) including an aperture such as aperture 54, which rotates rapidly enough to allow the laser and plasma radiation to pass therethrough, but to close before the debris arrives.

Figure 2:
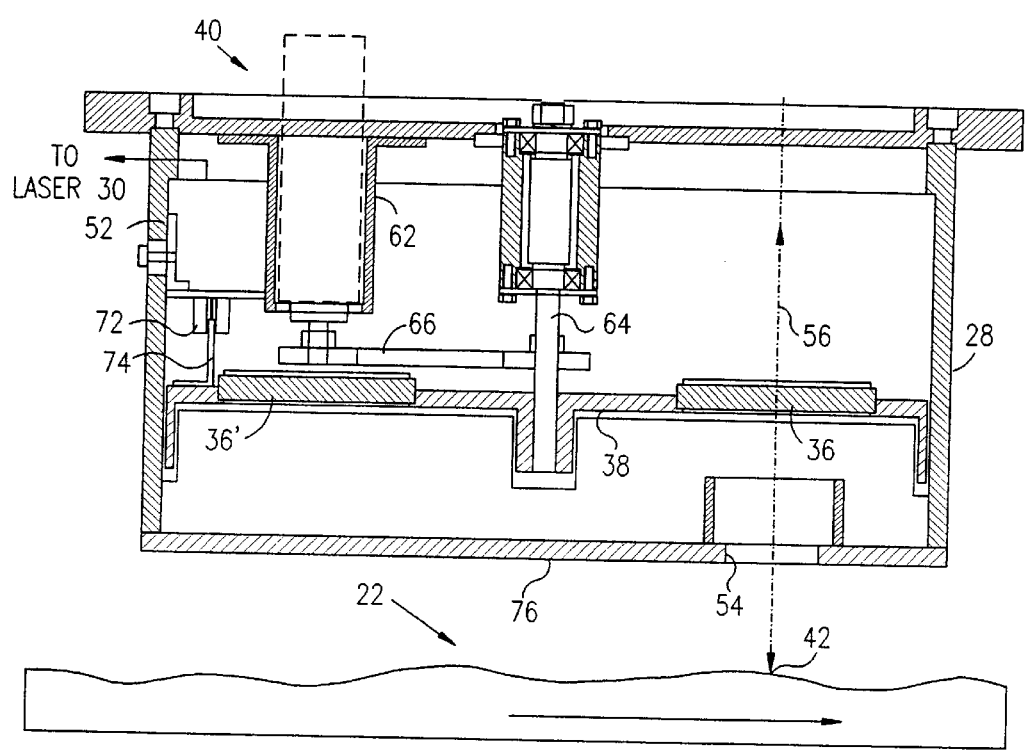
FIG. 2 is a schematic, sectional illustration of an optical assembly associated with the system of FIG. 1, in accordance with a preferred embodiment of the present invention.
Figure 3:
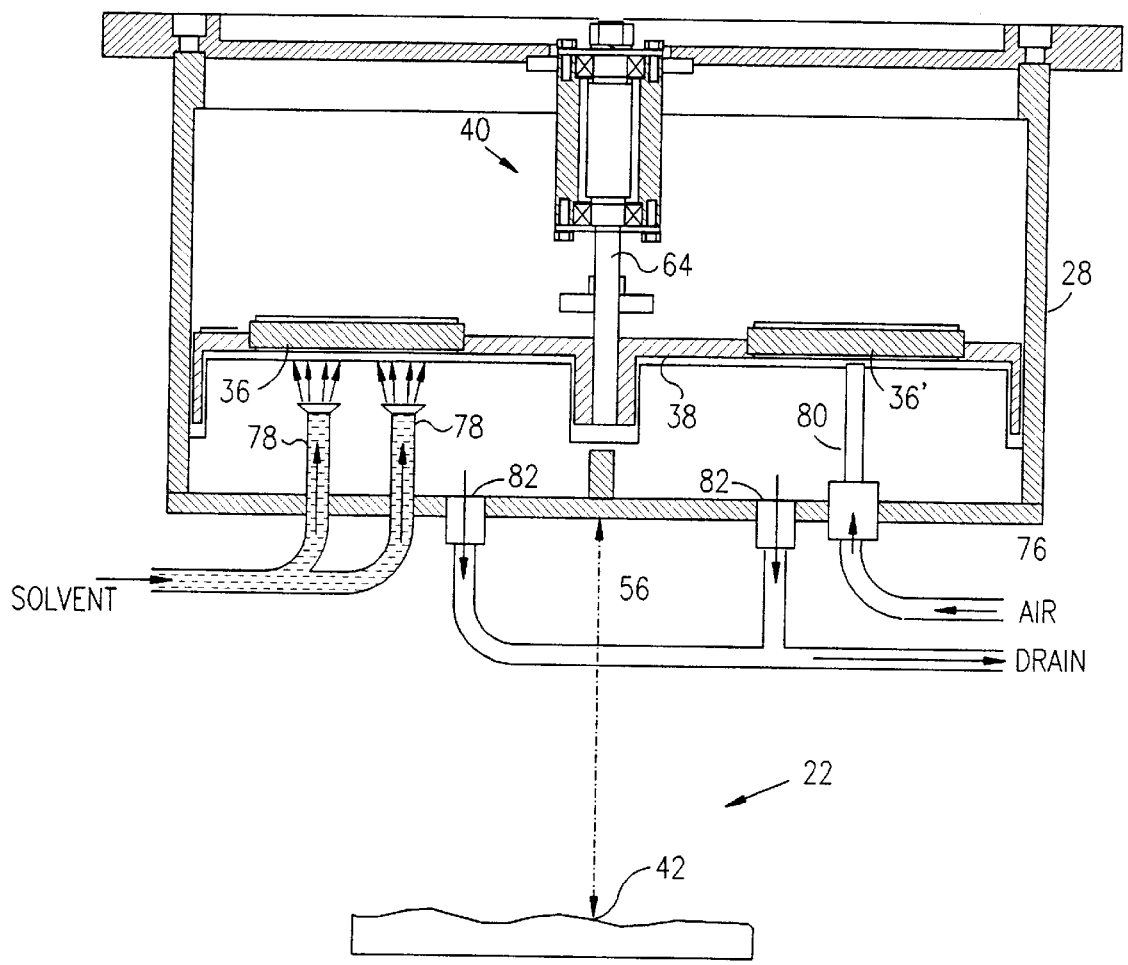
FIG. 3 is a schematic, sectional illustration of the optical assembly of FIG. 2, in a plane generally at right angles to that of FIG. 2.

Reference is now made to FIGS. 2, 3 and 4, which show details of optical assembly 28, in accordance with a preferred embodiment of the present invention. FIGS. 2 and 3 are schematic sectional views, wherein FIG. 2 shows a section in the plane of FIG. 1, and FIG. 3 shows a section in another vertical plane generally perpendicular to that of FIG. 2. FIG. 4 shows lower surface 76 of assembly 28 as seen from above.

As shown in FIG. 2, motor assembly 40 preferably comprises a motor 62, which drives a rotating shaft 64 on which turntable 38 is mounted. The motor is coupled to drive the shaft by a belt 66. An index 74 is mounted on turntable 38 adjacent to window 36', and a similar index (not shown for simplicity) may be mounted adjacent to window 36. When index 74 moves past a sensor 72, trigger 52 receives a signal from the sensor and sends the trigger pulse to laser 30, as described hereinabove. The laser then fires a pulse, which passes through window 36 to create the spark at point 42. Both plasma emission and debris pass back through aperture 54 to window 36.

As shown in FIG. 3, after the laser pulse, turntable 38 rotates by about 90°, to a position at which window 36 is opposite one or more fluid jets 78. The jets spray a solvent, preferably water, on the window surface to wash off the debris from sample 22. The solvent drains off the window through drain holes 82. Turntable 38 is then rotated through approximately another 180°, to a position opposite a gas jet 80, which dries optic 36, preferably using dry, clean air, such as "instrument air." The optic is then ready to return to the position shown in FIG. 2 for another laser shot. Window 36' goes through the same process as window 36, but 180° out of phase therewith.

Preferably, motor 62 operates intermittently, rotating turntable 38 in 180° steps and pausing at the washing and drying positions shown in FIG. 3. It is not necessary for the turntable to pause in the position shown in FIG. 2, since laser 30 can simply fire while the turntable is moving through this position.

FIG. 4 illustrates openings for fluid jets 78, gas jet 80 and drain holes 82 in lower surface 76 of optical assembly 28. In order to prevent the solvent from jets 78 from leaking through aperture 54 into sample 22, a low wall 84 separates washing and drying portions of surface 76. Additionally, a depression 86 is preferably formed around air jet 80 and drain hole 82 adjacent thereto, so that any residual solvent blown off the optics by the air jet runs into the drain.

Although assembly 28 is described hereinabove as a part of system 20, it will be appreciated that the principles of the present invention may similarly be applied to LIPS systems that are configured differently from the configuration shown in FIG. 1, as well as to other types of spectroscopic and optical detection systems that use pulsed radiation and/or operate in dirty environments. It will thus be understood that the preferred embodiments described above are cited by way of example, and the full scope of the invention is limited only by the claims.

I claim:

1. Apparatus for optical analysis of a sample, comprising:
    an energy source, which generates a pulse of energy that is incident on the sample, causing the sample to emit radiation characteristic of the composition of the sample;
    a detector assembly, which receives and analyzes the radiation emitted by the excited sample; and
    an optical assembly, which conveys the emitted radiation from the sample to the detector assembly, the optical assembly comprising:
        an optic proximal to the sample, on which optic the radiation is incident along a beam path thereof between the sample and the detector assembly; and
        a moving mechanical element, whose movement is synchronized with the pulse from the energy source so as to substantially prevent matter ejected from the sample responsive to the incident energy from accumulating on the optic.

2. Apparatus according to claim 1, wherein the moving mechanical element comprises a shutter, which is opened to allow the radiation to pass from the sample to the detector assembly, and which closes immediately following the pulse with sufficient speed so that the matter ejected from the sample substantially does not impinge on the optic.

3. Apparatus according to claim 2, wherein the shutter comprises a rotating platform, having an aperture which intercepts the beam path when the pulse is incident on the sample.

4. Apparatus according to claim 1, wherein the optical assembly comprises a cleaning device for cleaning the ejected matter from the optic, and wherein the moving mechanical element comprises a platform on which the optic is mounted and which positions the optic in proximity to the cleaning device after the pulse to remove the ejected matter therefrom.

5. Apparatus according to claim 4, wherein the platform rotates between an open position, in which the optic is positioned along the beam path, and a closed position, in which the optic is positioned in proximity to the cleaning device.

6. Apparatus according to claim 5, and comprising a trigger device, which senses that the platform is in the open position and sends a trigger signal to the energy source responsive thereto, causing the energy source to generate the pulse.

7. Apparatus according to claim 6, wherein the platform rotates continually between the open and closed positions, and the energy source generates a train of pulses responsive to the trigger signal and synchronized with the rotation of the platform.

8. Apparatus according to claim 4, wherein the cleaning device directs a solvent wash toward a surface of the optic on which the matter accumulates.

9. Apparatus according to claim 8, wherein the cleaning device dries the surface after the solvent wash.

10. Apparatus according to claim 1, wherein the energy source comprises a laser.

11. Apparatus for spectral analysis of a sample, comprising:
   an energy source, which generates a train of pulses of energy that is incident on the sample, causing the sample to emit radiation characteristic of the composition of the sample;
   a detector assembly, which receives and analyzes the radiation emitted by the excited sample;
   an optic proximal to the sample, on which optic the radiation is incident along a beam path thereof between the sample and the detector assembly; and
   a cleaning device, which removes matter ejected onto the optic from the sample due to the pulses, the cleaning device operating intermittently, between one pulse and the next in the pulse train.

12. Apparatus according to claim 11, wherein the cleaning device comprises a solvent wash, which is directed at a surface of the optic onto which the matter is ejected.

13. Apparatus according to claim 12, wherein the cleaning device dries the optic after the solvent wash.

14. Apparatus according to claim 11, and comprising a turntable on which the optic is mounted, which rotates in synchronization with the pulse train to move the optic between an open position in which the optic is positioned on the beam path and a closed position in which the optic is adjacent to the cleaning device.

15. A self-cleaning optical assembly for conveying energy along a beam path, comprising:
   a moving platform, having an open position and one or more closed positions;
   an optic mounted on the platform, so that in the open position, the optic intercepts the beam path; and
   a cleaning device, which cleans the optic when the platform is in the closed position.

16. An assembly according to claim 15, wherein the moving platform rotates about an axis therethrough, so as to cycle in alternation between the open and closed positions.

17. An assembly according to claim 16, wherein the rotation of the platform is synchronized with a pulsed energy source, which emits the energy along the beam path.

18. An assembly according to claim 17, and comprising a trigger device, which triggers the pulsed energy source responsive to the movement of the platform.

19. An assembly according to claim 15, wherein the cleaning device directs a solvent wash at a surface of the optic when the platform is in one of the closed positions.

20. An assembly according to claim 19, wherein the cleaning device dries the surface after the solvent wash.

21. An assembly according to claim 20, wherein the moving platform rotates continually between the open position, the closed position in which the solvent wash is directed at the surface, and another one of the one or more closed positions in which the cleaning device dries the surface.

22. An assembly according to claim 21, wherein the optic comprises two optics mounted on the platform in locations that are generally diametrically opposed, and wherein the assembly is configured so that while one of the optics is washed, the other is dried.

23. A method for spectral analysis of a sample, comprising:
   irradiating the sample with a pulse of energy, so that the sample emits radiation characteristic of the composition of the sample;
   collecting the radiation emitted by the sample along a beam path intercepting an optic; and
   moving an element in the beam path so as to prevent accumulation of matter ejected from the sample on the optic, wherein moving the element comprises moving an element in synchronization with the pulse of energy.

24. A method according to claim 23, wherein moving the element comprises moving a shutter to block the beam path to the optic after at least a portion of the radiation has passed therethrough but before the matter reaches the optic.

25. A method for spectral analysis of a sample, comprising:
   irradiating the sample with a pulse of energy, so that the sample emits radiation characteristic of the composition of the sample;
   collecting the radiation emitted by the sample along a beam path intercepting an optic; and
   moving an element in the beam path so as to prevent accumulation of matter ejected from the sample on the optic, wherein moving the element in the beam path comprises positioning the optic opposite a cleaning device and operating the cleaning device to remove the matter from the optic.

* * * * *